(12) United States Patent
Wolff et al.

(10) Patent No.: US 6,503,911 B2
(45) Date of Patent: Jan. 7, 2003

(54) SUSTAINED RELEASE RANOLAZINE FORMULATIONS

(75) Inventors: Andrew A. Wolff, San Francisco, CA (US); Fiona Baker, Dunfermline (GB); John Langridge, Wrexham (GB)

(73) Assignees: CV Therapeutics, Inc., Palo Alto, CA (US); Syntex USA, Inc., Palo Alto, CA (US)

( * ) Notice: Subject to any disclaimer, the term of this patent is extended or adjusted under 35 U.S.C. 154(b) by 0 days.

(21) Appl. No.: 10/041,521

(22) Filed: Oct. 19, 2001

(65) Prior Publication Data

US 2002/0090396 A1 Jul. 11, 2002

Related U.S. Application Data

(63) Continuation of application No. 09/538,337, filed on Mar. 29, 2000, which is a continuation of application No. 09/321,522, filed on May 27, 1999, now Pat. No. 6,303,607.
(60) Provisional application No. 60/099,804, filed on Sep. 10, 1998.

(51) Int. Cl.$^7$ ............................................... A61K 31/497
(52) U.S. Cl. .................................................. 514/252.13
(58) Field of Search ..................................... 514/252.12

(56) References Cited

U.S. PATENT DOCUMENTS 6,303,604 B1 * 10/2001 Wolff et al. ............ 514/252.12
6,369,062 B1 *  4/2002 Wolff et al. ............ 514/252.12

* cited by examiner

Primary Examiner—Jose G. Dees
Assistant Examiner—Konata M. George
(74) Attorney, Agent, or Firm—McDonnell Boehnen Hulbert & Berghoff

(57) ABSTRACT

A sustained release ranolazine formulation contains an intimate mixture of ranolazine and a partially neutralized pH-dependent binder to form a film that is mostly insoluble in aqueous media below pH 4.5 and soluble in aqueous media above pH 4.5. The formulation is suitable for twice daily administration of ranolazine and is useful for controlling the rate of dissolution of ranolazine, and to maintain human plasma ranolazine levels at between 550 and 7500 ng base/mL.

9 Claims, No Drawings

SUSTAINED RELEASE RANOLAZINE FORMULATIONS

This is a continuation of application Ser. No. 09/538,337 filed on Mar. 29, 2000 which is a continuation of U.S. patent application Ser. No. 09/321,522 filed on May 27, 1999 now U.S. Pat. No. 6,303,607, which claims priority to U.S. patent application Ser. No. 60/099,804 filed on Sep. 10, 1998.

BACKGROUND OF THE INVENTION

1. Field of the Invention

This invention relates to a method for using an orally administered sustained release ranolazine dosage formulations to maintain human ranolazine plasma levels at therapeutic levels.

2. Description of the Art

U.S. Pat. No. 4,567,264, the specification of which is incorporated herein by reference, discloses ranolazine, (±)-N-(2,6-dimethylphenyl)-4-[2-hydroxy-3-(2-methoxyphenoxy)-propyl]-1-piperazineacetamide, and its pharmaceutically acceptable salts, and their use in the treatment of cardiovascular diseases, including arrhythmias, variant and exercise-induced angina, and myocardial infarction.

U.S. Pat. No. 5,506,229, which is incorporated herein by reference, discloses the use of ranolazine and its pharmaceutically acceptable salts and esters for the treatment of tissues experiencing a physical or chemical insult, including cardioplegia, hypoxic or reperfusion injury to cardiac or skeletal muscle or brain tissue, and for use in transplants. Conventional oral and parenteral formulations are disclosed, including controlled release formulations. In particular, Example 7D of U.S. Pat. No. 5,506,229 describes a controlled release formulation in capsule form comprising microspheres of ranolazine and microcrystalline cellulose coated with release controlling polymers.

The presently preferred route of administration for ranolazine and its pharmaceutically acceptable salts and esters is oral. A typical oral dosage form is a compressed tablet, a hard gelatin capsule filled with a powder mix or granulate, or a soft gelatin capsule (softgel) filled with a solution or suspension. U.S. Pat. No. 5,472,707, the specification of which is incorporated herein by reference, discloses a high-dose oral formulation employing supercooled liquid ranolazine as a fill solution for a hard gelatin capsule or softgel.

As set forth in application Example 3, the initial trials of ranolazine on humans suffering from angina were failures. The trials used an immediate release of ranolazine formulation at a dose level of 120 mg taken three times daily. Based upon the initial experiments, it was uncertain whether or not ranolazine could be given to humans in an amount and mode that is effective against angina.

One problem with conventional oral dosage formulations is that they are not ideally suited to ranolazine and its pharmaceutically acceptable salts, because the solubility of ranolazine is relatively high at the low pH that occurs in the stomach. Furthermore ranolazine also has a relatively short plasma half-life. The high acid solubility property of ranolazine results in rapid drug absorption and clearance, causing large and undesirable fluctuations in plasma concentration of ranolazine and a short duration of action, thus necessitating frequent oral administration for adequate treatment.

There is therefore a need for a method for administering ranolazine in an oral dosage form once or twice daily that provides therapeutically effective plasma concentrations of ranolazine for the treatment of angina in humans.

SUMMARY OF THE INVENTION

In a first aspect, this invention is a sustained release ranolazine formulation where the majority of the formulation consists of active ranolazine.

In another aspect, this invention is a method of treating a human patient who is suffering from angina or other coronary disorders by administering a sustained release ranolazine formulation to the patient once or twice daily.

In yet another aspect, this invention is a method for treating a mammal having a disease state for which the administration of ranolazine is indicated, comprising the once or twice-daily administration of sustained release ranolazine formulation of this invention in a manner that maintains plasma ranolazine close to minimal effective levels without peak fluctuations.

Still another aspect of this invention is a method of maintaining useful levels of ranolazine in human plasma by administering a ranolazine containing dosage form only one or twice daily.

This invention includes methods for treating a human patient suffering from a cardiovascular disease selected from arrhythmias, variant and exercise-induced angina, and myocardial infarction. The method includes administering a sustained release pharmaceutical dosage form including at least 50% by weight ranolazine in no more than two tablets per dose to the human patient to maintain ranolazine plasma levels in the human patient of from about 550 to about 7500 ng base/mL for at least 24 hours wherein the dose is administered at a frequency selected from once, twice and three times over 24 hours.

This invention further includes methods for treating a human patient suffering from a cardiovascular disease selected from arrhythmias, variant and exercise-induced angina, and myocardial infarction. The method includes administering a sustained release pharmaceutical dosage form including from about 70 to about 80% by weight ranolazine in no more than two tablets per dose to the human patient to maintain ranolazine plasma levels in the human patient of from about 1000 to about 3900 ng base/mL for at least 24 hours wherein the dose is administered at a frequency selected from one and two times over 24 hours.

This invention also includes pharmaceutical dosage forms comprising at least about 50 wt % ranolazine and at least one pH dependent binder that inhibits the release of ranolazine from the sustained release dosage form when the sustained release dosage form is subjected to an aqueous environment having a pH of the stomach and that promotes the release of a therapeutic amount of ranolazine in an aqueous solution having a pH above about 4.5.

DETAILED DESCRIPTION OF THE INVENTION

"Ranolazine" is the compound (±)-N-(2,6-dimethylphenyl)-4-[2-hydroxy-3-(2-methoxphenoxy)propyl]-1-piperazine-acetamide, or its enantiomers (R)-(+)-N-(2,6-dimethylphenyl)-4-[2-hydroxy-3-(2-methoxyphenoxy)-propyl]-1-piperazineacetamide, and (SH)-(−)-N-2,6-dimethylphenyl)-4-[2-hydroxy-3-(2-methoxyphenoxy)-propyl]-1-piperazineacetamide and their pharmaceutically acceptable salts, and mixtures thereof. Unless otherwise stated the ranolazine plasma concentrations used in the specification and examples refers to ranolazine free base.

"Optional" and "optionally" mean that the subsequently described event or circumstance may or may not occur, and that the description includes instances where the event or circumstance occurs and instances in which it does not. For example, "optional pharmaceutical excipients" indicates that a formulation so described may or may not include pharmaceutical excipients other than those specifically stated to be present, and that the formulation so described includes instances in which the optional excipients are present and instances in which they are not.

"Treating" and "treatment" refer to any treatment of a disease in a mammal, particularly a human, and include:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

"Immediate release" ("IR") refers to formulations or dosage units that rapidly dissolve in vitro and are intended to be completely dissolved and absorbed in the stomach or upper gastrointestinal tract. Conventionally, such formulations release at least 90% of the active ingredient within 30 minutes of administration.

"Sustained release" ("SR") refers to formulations or dosage units of this invention that are slowly and continuously dissolved and absorbed in the stomach and gastrointestinal tract over a period of about six hours or more. Preferred sustained release formulations are those exhibiting plasma concentrations of ranolazine suitable for no more than twice daily administration with two or less tablets per dosing as described below.

Plasma ranolazine concentration is a mean concentration determined by analyzing the concentration of ranolazine in as few as five to as many as ten humans who are on the same dosing schedule. It is important that the ranolazine concentration is a mean value because of variances in ranolazine concentrations in individuals that may be caused by differences in weight, metabolism, or disease states which may cause one person to metabolize ranolazine faster or slower than an average person. The plasma ranolazine levels are determined from drawn blood onto heparin.

Definitions of other terms used in this application are:

ANOVA=analysis of variance

ATP=adenosine triphosphate

ECG=electrocardiographic

ETT=exercise treadmill test

PDH=pyruvate dehydrogenase $C_{max}$=maximum concentration $C_{trough}$=residual concentration at 8 hours post-dose for IR formulations and 12 hours post-dose for SR formulations A–C of Example 2.

tid=three times per day bid=twice daily $C_x$=concentration at time x $T_{max}$=time to maximum concentration $AUC_x$=area under the curve after x hours or time interval Percentages given are percentages by weight, unless otherwise stated. This invention involves sustained release ranolazine dosage forms as well as methods for administering sustained release ranolazine dosage forms of this invention to provide for therapeutic plasma levels of ranolazine.

The sustained release ranolazine formulations of this invention are preferably in the form of a compressed tablet comprising an intimate mixture of ranolazine and a partially neutralized pH-dependent binder that controls the rate of ranolazine dissolution in aqueous media across the range of pH in the stomach (typically approximately 2) and in the intestine (typically approximately about 5.5).

To provide for a sustained release of ranolazine, one or more pH-dependent binders are chosen to control the dissolution profile of the ranolazine formulation so that the formulation releases ranolazine slowly and continuously as the formulation passed through the stomach and gastrointestinal tract. The dissolution control capacity of the pH-dependent binder(s) is particularly important in a sustained release ranolazine formulation because a sustained release formulation that contains sufficient ranolazine for twice daily administration may cause untoward side effects if the ranolazine is released too rapidly ("dose-dumping").

Accordingly, the pH-dependent binders suitable for use in this invention are those which inhibit rapid release of drug from a tablet during its residence in the stomach (where the pH is-below about 4.5), and which promotes the release of a therapeutic amount of ranolazine from the dosage form in the lower gastrointestinal tract (where the pH is generally greater than about 4.5). Many materials known in the pharmaceutical art as "enteric" binders and coating agents have the desired pH dissolution properties. These include phthalic acid derivatives such as the phthalic acid derivatives of vinyl polymers and copolymers, hydroxyalkylcelluloses, alkylcelluloses, cellulose acetates, hydroxyalkylcellulose acetates, cellulose ethers, alkylcellulose acetates, and the partial esters thereof, and polymers and copolymers of lower alkyl acrylic acids and lower alkyl acrylates, and the partial esters thereof.

Preferred pH-dependent binder materials which can be used in conjunction with ranolazine to create a sustained release formulation are methacrylic acid copolymers. Methacrylic acid copolymers are copolymers of methacrylic acid with neutral acrylate or methacrylate esters such as ethyl acrylate or methyl methacrylate. A most preferred copolymer is methacrylic acid copolymer, Type C, USP (which is a copolymer of methacrylic acid and ethyl acrylate having between 46.0% and 50.6% methacrylic acid units). Such a copolymer is commercially available, from Röhm Pharma as Eudragit® L 100–55 (as a powder) or L30D-55 (as a 30% dispersion in water). Other pH-dependent binder materials which may be used alone or in combination in a sustained release ranolazine dosage form include hydroxypropyl cellulose phthalate, hydroxypropyl methylcellulose phthalate, cellulose acetate phthalate, polyvinylacetate phthalale, polyvinylpyrrolidone phthalate, and the like. One or more pH-dependent binders are present in the ranolazine dosage forms of this invention in an amount ranging from about 1 to about 20 wt %, more preferably from about 5 to about 12 wt % and most preferably about 10 wt %.

One or more pH-independent binders may be in used in sustained release ranolazine oral dosage forms. It is to be noted that pH-dependent binders and viscosity enhancing agents such as hydroxypropyl methylcellulose, hydroxypropyl cellulose, methylcellulose, polyvinylpyrrolidone, neutral poly(meth)acrylate esters, and the like, do not themselves provide the required dissolution control provided by the identified pH-dependent binders. The pH-independent binders are present in the formulation of this invention in an amount ranging from about 1 to about 10 wt %, and preferably in amount ranging from about 1 to about 3 wt % and most preferably about 2.0 wt %.

As shown in Table 1, ranolazine is relatively insoluble in aqueous solutions having a pH above about 6.5, while the solubility begins to increase dramatically below about pH 6.

TABLE 1

| Solution pH | Solubility (mg/mL) | USP Solubility Class |
|---|---|---|
| 4.81 | 161 | Freely soluble |
| 4.89 | 73.8 | Soluble |
| 4.90 | 76.4 | Soluble |
| 5.04 | 49.4 | Soluble |
| 5.35 | 16.7 | Sparingly soluble |
| 5.82 | 5.48 | Slightly soluble |
| 6.46 | 1.63 | Slightly soluble |
| 6.73 | 0.83 | Very slightly soluble |
| 7.08 | 0.39 | Very slightly soluble |
| 7.59 (unbuffered water) | 0.24 | Very slightly soluble |
| 7.73 | 0.17 | Very slightly soluble |
| 12.66 | 0.18 | Very slightly soluble |

Increasing the pH-dependent binder content in the formulation decreases the release rate of ranolazine from the formulation at pH is below 4.5 typical of the pH found in the stomach. The enteric coating formed by the binder is less soluble and increases the relative release rate above pH 4.5, where the solubility of ranolazine is lower. A proper selection of the pH-dependent binder allows for a quicker release rate of ranolazine from the formulation above pH 4.5, while greatly affecting the release rate at low pH. Partial neutralization of the binder facilitates the conversion of the binder into a latex like film which forms around the individual ranolazine granules. Accordingly, the type and the quantity of the pH-dependent binder and amount of the partial neutralization composition are chosen to closely control the rate of dissolution of the ranolazine from the formulation.

The dosage forms of this invention should have a quantity of pH-dependent binders sufficient to produce a sustained release formulation from which the release rate of ranolazine is controlled such that at low pHs (below about 4.5) the rate of dissolution is significantly slowed. In the case of methacrylic acid copolymer, type C, USP (Eudragit® L 100–55), a suitable quantity of pH-dependent binder is between 5% and 15%. The pH dependent binder will typically have from about 1 to about 20% of the binder methacrylic acid carboxyl groups neutralized. However, it is preferred that the degree of neutralization ranges from about 3 to 6%.

The sustained release formulation may also contain pharmaceutical excipients intimately admixed with the ranolazine and the pH-dependent binder. Pharmaceutically acceptable excipients may include, for example, pH-independent binders or film-forming agents such as hydroxypropyl methylcellulose, hydroxypropyl cellulose, methylcellulose, polyvinylpyrrolidone, neutral poly(meth)acrylate esters (e.g. the methyl methacrylate/ethyl acrylate copolymers sold under the trademark Eudragit® NE by Röhm Pharmal, starch, gelatin, sugars, carboxymethylcellulose, and the like. Other useful pharmaceutical excpients include diluents such as lactose, mannitol, dry starch, microcrystalline cellulose and the like; surface active agents such as polyoxyethylene sorbitan esters, sorbitan esters and the like; and coloring agents and flavoring agents. Lubricants (such as talc and magnesium stearate) and other tableting aids are also optionally present.

The sustained release ranolazine formulations of this invention have a ranolazine content of above about 50% by weight to about 95% or more by weight, more preferably between about 70% to about 90% by weight and most preferably from about 70 to about 80% by weight; a pH-dependent binder content of between 5% and 40%, preferably between 5% and 25%, and more preferably between 5% and 15%; with the remainder of the dosage form comprising pH-independent binders, fillers, and other optional excipients.

Particularly preferred sustained release ranolazine formulations of this invention consist, essentially of:

| Ingredient | Weight Range (%) | Preferred Range (%) | Most Preferred (%) |
|---|---|---|---|
| Ranolazine | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release ranolazine formulations of this invention are prepared as follows: ranolazine and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting ranolazine containing tablets may be coated with an optional film-forming agent, for identification, taste-masking purposes and to improve ease of swallowing. The film forming agent will typically be present in an amount ranging from between 2% and 4% of the tablet weight. Suitable film-forming agents are well-known to the art and include hydroxypropyl methylcellulose, cationic methacrylate copolymers (dimethylaminoethyl methacrylate/methylbutyl methacrylate copolymers-Eudragit® E-Röhm Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of ranolazine in the tablet. The tablets will include from 300 to 1100 mg of ranolazine free base. Preferably, the tablets will include amounts of ranolazine free base ranging from 400–600 mg, 650–850 mg, and 900–1100 mg.

In order to influence the dissolution rate, the time during which the ranolazine containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Surprisingly, it has been found that these methods produce sustained release ranolazine formulations that provide lower peak plasma ranolazine levels and yet effective plasma concentrations of ranolazine for up to 12 hours and more after administration, when the ranolazine used as its free base, rather than as the more pharmaceutically common ranolazine dihydrochloride salt or as another salt or ester. The use of ranolazine free base affords at least one advantage: The proportion of ranolazine in the tablet can be increased, since the molecular weight of ranolazine free base is only 85% that of ranolazine dihydrochloride. In this manner, delivery of an effective amount of ranolazine is achieved while limiting the physical size of the dosage unit.

Another advantage of sustained release ranolazine formulations of this invention is that they are prepared by a process that essentially involves only water as a solvent, and utilizes standard pharmaceutical processing techniques and equipment.

The sustained release ranolazine formulations of this invention can be used for treating cardiovascular diseases, including arrhythmias, variant and exercise-induced angina, and myocardial infarction; treatment of tissues experiencing a physical or chemical insult, including cardioplegia, hypoxic or reperfusion injury to cardiac or skeletal muscle or brain tissue, and ischemia; and peripheral arterial diseases, such as intermittent claudication. It is most preferred that the sustained release dosage formulation be used as a mammalian anti-anginal agent and most preferably as a human anti-anginal agent.

The oral sustained release ranolazine dosage formulations of this invention are administered one, twice; or three times in a 24 hour period in order to maintain a plasma ranolazine level above the threshold therapeutic level and below the maximally tolerated levels, of between about 550 and 7500 ng base/mL in a patient. This corresponds to an amount of ranolazine 2 HCl ranging from about 644 ng/mL to about 8782 ng/mL. Furthermore, the timing of the oral ingestion of the ranolazine oral dosage forms should be controlled to insure that the plasma ranolazine level does not exceed about 7500 ng base/mL and preferably so that the plasma ranolazine level does not exceed about 5000 ng base/mL an most preferably so that is does not exceed 3800 ng base/mL. In some instances it may be beneficial to limit the peak plasma ranolazine level to no more than about ng base/mL At the same time, the plasma trough ranolazine levels should preferably not fall below about 1000 ng base/mL, and in some instances should not fall below 1700 ng base/mL In order to achieve the preferred plasma ranolazine level of from about 1000 to about 3800 ng base/mL, it is preferred that the oral ranolazine dosage forms described herein are administered once or twice daily. If the dosage forms are administered twice daily, then it is preferred that the oral ranolazine dosage forms are administered at about twelve hour intervals.

In addition to formulating and administering oral sustained release dosage forms of this invention in a manner that controls the plasma ranolazine levels, it is also important to minimize the difference between peak and trough plasma ranolazine levels. The peak plasma ranolazine levels are typically achieved at from about 30 minutes to eight hours or more after initially ingesting the dosage form while trough plasma ranolazine levels are achieve at about the time of ingestion of the next scheduled dosage form. It is preferred that the sustained release dosage forms of this invention are administered in a manner that allows for a peak ranolazine level no more than 8 times greater than the trough ranolazine level, preferably no more than 4 times greater than the trough ranolazine and most preferably no greater than 2 times trough ranolazine level.

The sustained release ranolazine formulations of this invention provide the therapeutic advantage of minimizing variations in ranolazine plasma concentration while permitting, at most, twice-daily administration. The formulation may be administered alone, or (at least initially) in combination with an immediate release formulation if rapid achievement of a therapeutically effective plasma concentration of ranolazine is desired or by soluble IV formulations and oral dosage forms.

The following Examples are representative of the invention, but are not to be construed as limiting the scope of the claims.

EXAMPLES

These Examples detail methods for manufacturing ranolazine dosage forms as well as experiments performed to evaluate the effectiveness of ranolazine administration and effectiveness. Throughout these Examples it should be noted that:

(1) Oral doses of the instant release (IR) formulation were given as capsules or tablets of the dihydrochloride salt and are expressed as the dihydrochloride salt.

(2) Oral doses of the sustained release (SR) formulation were given as tablets of the ranolazine base and are expressed as the base.

(3) When IR and SR formulations were compared in the same study, doses are expressed in terms of both base and dihydrochloride. The conversion factor for dihydrochloride to base is 0.854 (e.g.: 400 mg dihydrochloride×0.854=342 mg free base equivalent).

(4) All plasma levels and pharmacokinetic parameters are expressed as levels of free base.

Example 1

This Example describes a method of preparing immediate release (IR) ranolazine formulations. Ranolazine dihydrochloride (4000 g), microcrystalline cellulose (650 g), polyvinylpyrrolidone (100 g), and croscarmellose sodium (100 g) powders were intimately mixed together in a Fielder PMA 65 mixer-granulator, and sufficient water was then added, with mixing to form a granulate. The granulate was dried in an Aeromatic Strea-5 fluid bed drier, screened, and mixed with magnesium stearate (100 g). The mixture was filled into hard gelatin capsules to a fill weight of, for example, 500 mg per capsule to achieve a dose of 400 mg of ranolazine dihydrochloride (equivalent to 342 mg of ranolazine free base) per capsule, but may be filled to fill weight of 30 to 400 mg of ranolazine dihydrochloride.

Example 2

This Example describes a method of preparing sustained release (SR) ranolazine formulations.

A sustained release (SR) formulation, designated as SR Formulation A, and including pH-dependent and pH-independent binders was prepared by combining Ranolazine (2500 g), methacrylic acid copolymer, Type C (Eudragit® L 100–55-Röhm Pharma) (1000 g), microcrystalline cellulose (Avicel®) (100 g) (710 g), and polyvinyl pyrrolidinone powders were intimately mixed together in a Fielder PMA 65 mixer-granulator. The mixture was granulated with a solution of sodium hydroxide (40 g) in water, and a 30% aqueous dispersion of methyl methacrylate/ethyl acrylate copolymer (Eudragit NE 30 D-Röhm Pharma) (1667 g) was added to the wet mass. The resulting granulate was dried in an Aeromatic Strea-5 fluid bed drier, screened, and then mixed with croscarmellose sodium (100 g) and magnesium stearate (50 g). The mixture was compressed into 684 mg tablets with a Manesty B tablet press to achieve dose of 342 mg of ranolazine free base per tablet. This formulation is referred to as SR Formulation A.

SR Formulation B was prepared in the same manner as SR Formulation A except that the Eudragit® L 100–55 was reduced to 500 g, and the Eudragit® NE 30 D was replaced by a 40% aqueous dispersion of a methyl methacrylate/ethyl acrylate copolymer (Eudragit® NE 40 D-Röhm Pharma) (2500 g). The resulting (SR) formulation included 342 mg ranolazine free base per tablet.

In SR Formulation C, ranolazine free base (342 mgs) was blended with microcrystalline cellulose and polyvinyl pyrrolininone K25, granulated with water, dried, and blended with croscarmellose sodium and magnesium stearate. The blend was compressed into tablets and coated with an enteric coating.

SR Formulation D, including only a pH dependent binder was prepared by combining Ranolazine (7500 g), Eudragit® L 100–55 (1000 g), hydroxypropyl methylcellulose (Methocel(® E5—source) (200 g), and microcrysalline cellulose (Avicel®) (1060 g) by intimate mixing. The mixed powders were granulated with a solution of sodium hydroxide (40 g) in water (1900 to 2500 grams). The granulate was dried and screened, mixed with magnesium stearate (200 g), and compressed for example into tablets weighing 667 mg to achieve a dose of 500 mg of ranolazine free base per tablet. The tablets were spray coated in a 24 inch Accelacota® cylindrical pan coater with OPADRY film coating solution to a 2–4% weight gain. OPADRY film coating solutions are available in a variety of colors from Colorcon, West Point, Pa.

The stepwise procedure for preparing SR Formulation D is as follows:

a) Blend together ranolazine, microcrystalline cellulose, methacrylate copolymer (Type C) and hydroxypropyl methyl cellulose using an appropriate blender.

b) Dissolve sodium hydroxide in purified water.

c) Using appropriate granulation equipment, slowly add the sodium hydroxide solution to the blend with constant mixing. Add a further aliquot of water, if necessary.

d) Continue mixing to achieve additional massing. Add a further aliquot of water, if necessary.

e) Dry granulated in a fluid bed dryer.

f) Screen dried granules through an appropriate mill.

g) Add magnesium stearate to the screened granules and blend together.

h) Pass the granulated material through a chilsonator, if needed.

i) Compress the granules into tablets using appropriately sized tooling.

j) Disperse OPADRY powder in water and film-coat using appropriately sized coating equipment to a typical level of 2–4% by weight.

k) Polish with carnauba wax using a typical level of 0.002–0.003% by weight.

Example 3

This Example summarizes a study published in *Circulation* 90:726–734 (1994) that demonstrated that ranolazine was ineffective as an antianginal and anti-ischemic agent when administered as an IR formulation of Example 1.

Patients with stable angina pectoris took part in the study. Any previous antianginal drugs used by the patients were discontinued under medical supervision. Three hundred nineteen patients received single-blind placebo for up to 18 days, and 318 stopped exercise because of angina of moderate severity, had evidence of myocardial ischemia ($\geq$1-mm ST segment depression), and were randomized to one of four study groups and administered; ranolazine ●2HCl 30 mg tid (n=81); ranolazine ●2HCl 60 mg tid (n=81); ranolazine ●2HCl 120 mg tid (n=78);, and placebo tid (n=79). After administration of 30-, 60- and 120-mg doses tid, the mean peak plasma concentrations of ranolazine free base at 1 hour after dose were 94, 219 and 510 ng/mL, respectively, and the mean trough plasma concentrations at 8 hours after dose were 18, 37 and 90 ng/mL, respectively.

After the 4-week double-blind phase, symptom-limited exercise tests were repeated at 1 hour (peak test) and 8 hours (trough test) after the study medication was administered. Total exercise duration at baseline ($\pm$SEM) was 5.9$\pm$0.2 minutes for the placebo group and 6.4$\pm$0.3, 5.9$\pm$0.3, and 6.6$\pm$0.2 minutes for the ranolazine 30-, 60-, and 120-mg groups, respectively (P=NS). After 4 weeks of double-blind therapy, compared with baseline values, at 1 hour after the study medication was administered (peak effect), total exercise duration ($\pm$SEM) increased by 0.45$\pm$0.2 minutes in the placebo group and by 0.3$\pm$0.2, 0.6$\pm$0.2, and 0.5$\pm$0.2 minutes in the ranolazine 30-, 60- and 120-mg groups, respectively (placebo versus ranolazine, P=NS). Times to 1-mm ST-segment depression at baseline were similar in the four groups and, after 4 weeks of therapy in each group, increased significantly by similar magnitudes at 1 hour after the administration of the medications. Similar changes were seen for the time to onset of angina. Eight hours after administration (trough effect), no differences in total exercise time or any other exercise variables were observed between the placebo and the ranolazine groups. Compared with the baseline values, the number of anginal attacks per week and the number and duration of ischemic episodes per 48 hours during Holter monitoring decreased significantly by similar magnitudes in the placebo and ranolazine groups.

These results indicated that therapy with ranolazine.2HCl 30, 60 and 120 mg tid was not superior to placebo. The study also did not show beneficial effects of similar doses of ranolazine on either mycocardial ischema or exercise performance or on anginal attacks during daily life in patients with angina pectoris.

Example 4

In this Example, the safety and anti-ischemic effects of high plasma ranolazine levels in a large group of angina patients was evaluated and the duration of any effects during steady-state dosing with bid and tid regimens was assessed. In this Example, patients with chronic stable angina pectoris who were responsive to conventional antianginal drugs were treated with 3 ranolazine●2HCl dosing regimens: 267 mg tid, 400 mg bid and 400 mg tid IR Formulations of Example 1. Exercise testing parameters and ranolazine free base concentrations were determined at peak and trough plasma levels.

Methods

The study involved double-blind, placebo-controlled randomized treatment phase with 4 treatments (placebo, ranolazine●2HCl 400 mg bid, ranolazine ●2HCl 267 mg tid, and ranolazine●2HCl 400 mg tid), 4 treatment sequences and 5 double-blind treatment periods in an extended period Latin square design on pre-qualified patients who were responsive to known antianginal therapy and had stable exercise times.

Human patients with chronic stable angina pectoris, of at least 3 months' duration, that had responded to conventional antianginal therapy were considered candidates. In addition, patients had to have electrocardiogrpahic (ECG) evidence of exercise-induced ischemia based upon horizontal or down-sloping ST-segment depression of $\geq$1 mm that persisted in 3 consecutive beats during an exercise stress test and an ECG pattern that would not interfere with interpretation of ST-segment changes. The latter criterion specifically excluded patients with left ventricular hypertrophy, preexcitation, conduction abnormalities, or pacemaker rhythm. Other exclusion criteria included unstable angina or myocardial infarction within the preceding 3 months, heart failure defined as New York Heart Association Class III or IV, significant valvular or congenital heart disease that was uncorrected, need for digoxin or long-acting nitrate therapy, labile diabetes mellitus, or other serious conditions that would confuse follow-up evaluation.

These immediate release ranolazine .2HCl dosing regimens (267 mg tid, 400 mg bid, 400 mg tid) and a placebo were administered during the treatment phase. Patients took one capsule containing either 267 mg or 400 mg of ranolazine dihydrochloride, or placebo at 8:00 a.m., 4:00 p.m., 8:00 p.m. and 12:00 a.m. All capsules were identical in appearance. Patients were randomized to 1 of 4 treatment sequences, with 25% of the patients assigned to each sequence. Each treatment was administered for 1 week, with one treatment repeated during a fifth 1-week period.

To qualify patients receiving their usual antianginal medications underwent a screening exercise treadmill test (ETT-1) using a Sheffield modified Bruce protocol. If the time to onset angina was $\geq 3$ but $\geq 13$ minutes, an antianginal drug was withdrawn and treatment with single-blind placebo was initiated. After 1 to 2 weeks, patients returned for another ETT (ETT-2). If the time to onset angina decreased by 1 minute compared with ETT-1, the patient was considered to have completed the first qualifying ETT. If the decrease in time to onset angina was not $\geq 1$ minute, a second antianginal drug could be withdrawn and the above sequence repeated. If necessary, a third antianginal drug could be withdrawn according to this procedure in order for the patient to qualify. Long-acting nitrates were always withdrawn first; beta-blockers; and calcium antagonists could be withdrawn in either order from patients not receiving long-acting nitrates. After the patient achieved the first qualifying ETT (ETT-2), a second qualifying ETT (ETT-3) was performed in which the time to onset angina had to be within ±15% of that observed during ETT-2. In addition, each of the qualifying ETTs had to have ECG signs of ischemia ($\geq 1$ mm horizontal or down-sloping ST-segment depression in 3 consecutive beats). Patients meeting these criteria were used in the study.

After each 1 week period, patients returned to the exercise laboratory in the morning, at least 1 hour after a light breakfast, for an ETT. This was designated the trough ETT; the trough ETTs were performed at the same time of day for each patient. After completing the trough ETT, the patient received the next scheduled blinded medication dose from the blister pack used that week. Another ETT was performed 1 hour after the administered dose. This was designated the peak ETT. Blood samples were obtained at trough (approximately 8 hours after dosing) and at peak (1 hour after dosing). Other standard laboratory tests were monitored regularly throughout the study.

Blood pressure (by cuff) and heart rate were monitored before all ETTs, during the ETT, during the last minute of each stage of the test, at onset angina, at the point of maximum exercise, and during recovery (every minute for 4 minutes, then every 5 minutes until values returned to baseline). Heart rates also was monitored continuously and standard 12-lead ECG recordings were done immediately before exercise with the patient standing on the treadmill, at the end of each stage of exercise, at the maximally tolerated exercise load, and at the termination of exercise.

Mean treadmill exercise times for the 3 exercise variables of interest during placebo and the different ranolazine dosing regimens (ranolazine-placebo) for all patients at peak and trough are summarized in Table 2 below.

TABLE 2

Exercise Test Data for All Patients at Peak and Trough

| Mean Exercise Variable (all patients, minutes) | | Double-blind Placebo | Ranolazine 400 mg bid | Ranolazine 267 mg tid | Ranolazine 400 mg tid |
|---|---|---|---|---|---|
| Time to onset angina | Peak | 9.01 | 9.33 | 9.40 | 9.33 |
| | Trough | 8.58 | 8.77 | 8.78 | 8.65 |
| Exercise Duration | Peak | 10.67 | 10.83 | 10.87 | 10.84 |
| | Trough | 10.50 | 10.55 | 10.56 | 10.60 |
| Time to 1 mm ST depression | Peak | 9.58 | 9.86 | 9.99 | 9.94 |
| | Trough | 9.04 | 9.22 | 9.22 | 9.31 |

At peak ranolazine plasma concentrations, all ETT ischemia parameters were prolonged over placebo and most notably, the time to onset of 1-mm ST-segment depression. In the all-patients analysis, the increase in time to onset angina over placebo ranged from 0.32 to 0.39 minutes ($p \leq 0.01$) and time to onset of 1-mm ST-segment depression ranged from 0.28 to 0.41 minutes ($p \leq 0.02$) for each of the 3 ranolazine dosing regimens and all regimens combined. Also, the total duration of exercise was significantly increased for all regimens combined and trends of similar direction and magnitude were noted for each dosing regimen. In the per-protocol analysis each of the 3 ETT parameters were prolonged ($p \leq 0.01$) for all ranolazine dosing regimens combined. All individual ranolazine dosing regimens significantly prolonged time to 1-mm ST-segment depression and nonsignificant trends of similar direction and proportions were found for time to onset angina and duration of exercise. In general, results of the per-protocol analysis, except that the magnitude of the effect appeared to somewhat greater in those with monotherapy.

At trough plasma concentrations, ranolazine had a lesser effect on ETT parameters. The results for the all-patients and per-protocol analyses were relatively consistent, demonstrating trends to increased exercise times. But only the time to 1 mm ST-segment depression for all ranolazine regimens combined in the all-patients analysis achieved statistical significance.

In view of the more pronounced increases in exercise parameters observed with ranolazine monotherapy, the responses to ranolazine among patients receiving different concomitant antianginal medications were analyzed. These post-hoc analyses were performed on peak ranolazine data, when the effects to improve exercise times were most evident. Because long-acting nitrates were withdrawn first during the single-billed qualifying phase, no patient entered double-blind treatment receiving long-acting nitrates.

Of patients with peak efficacy data, 34% (107/312) of the patients received beta-blockers during double-blind treatment and 24% (75/312) received calcium antagonists.

Exercise test parameters improved at peak ranolazine concentrations (ranolazine-placebo) whether or not patients were receiving beta-blockers. These improvements were slightly larger in magnitude in the 205 patients not receiving beta-blockers compared to the 107 patients who received beta-blockers. But the differences between those receiving beta-blockers and those not receiving them did not achieve statistical significance for any exercise parameter. In patients not receiving beta-blockers, all exercise parameters improved significantly on each of the 3 ranolazine regimens, and also with all ranolazine regimens combined. Similar trends were observed in the smaller number of patients receiving beta-blockers. Analyses of exercise data from patients taking calcium antagonists compared with those not receiving calcium antagonists produced similar findings.

Table 3 below summarizes the mean peak and trough plasma ranolazine concentrations, in terms of ranolazine dihydrochloride base, for all patients by gender and for each dosing regimen.

TABLE 3

Mean (± Standard Deviation) Ranolazine
Plasma Concentrations by Dosing Regimen

|  | Ranolazine 400 mg bid | Ranolazine 267 mg tid | Ranolazine 400 mg tid |
|---|---|---|---|
| Peak (ng/mL) | | | |
| All Patients | 1882 (1094) | 1346 (823) | 2128 (1198) |
| Males | 1762 (999) | 1261 (774) | 1917 (1046) |
| Females | 2171 (1253) | 1594 (904) | 2654 (1385) |
| Trough (ng/mL) | | | |
| All Patients | 235 (288) | 316 (336) | 514 (500) |
| Males | 235 (264) | 316 (336) | 518 (494) |
| Females | 235 (342) | 316 (340) | 505 (517) |

The plasma mean peak concentrations ranged from 1346 to 2128 ng per mL ranolazine free base. The 400 mg tid dosing regimen was associated with the highest ranolazine plasma concentrations. Mean trough ranolazine plasma concentrations ranged from 235 to 514 ng per mL. Mean peak ranolazine plasma concentrations were somewhat higher in females than in males, but there were no sex differences in plasma concentrations evident in trough.

At peak ranolazine plasma concentrations, there were no statistically significant differences among any of the ranolazine dosing regimens and placebo for double product. Likewise, at trough ranolazine plasma concentrations, there were no statistically significant differences among the 3 ranolazine dosing regimens and placebo in the per-protocol analysis for standing or maximum exercise double product.

The results of this study suggest that ranolazine is an effective antianginal and anti-ischemic compound in patients with chronic stable angina pectoris. At peak plasma concentrations, the three ranolazine dosing regimens used prolonged time to onset of angina and duration of exercise as well as time to 1-mm ST-segment depression on average about 0.33 minutes over that observed with placebo. Improvement in exercise parameters was observed in the present study not only in patients receiving concomitant antianginal therapy (eg, beta-blockers and calcium antagonists), but also in the subgroup who received only ranolazine monotherapy. In the latter patients, the treatment effect appeared to be somewhat greater in magnitude. This suggests that ranolazine also may be useful in monotherapy in patients with chronic stable angina pectoris.

The hemodynamic findings indicate that the improvement in exercise parameters in peak ranolazine plasma concentrations was not associated with changes in blood pressure or heart rate. The nonhemodynamic mechanism of action of ranolazine, therefore, differs from that of other antianginal drugs in current clinical use.

Most important, we documented that the antianginal and anti-ischemic effects of the immediate-release ranolazine preparation studied did not persist throughout the dosing interval. Although time to onset of ischemic-type ST-segment depression was significantly prolonged and trends of similar direction were noted for other ETT parameters, the effect was minimal at trough ranolazine plasma concentrations. Mean peak ranolazine free base plasma concentrations ranged from 1346 to 2128 ng per mL, while mean trough plasma concentrations ranged from 235 to 514 ng per mL. It seems evident that the higher mean ranolazine plasma concentrations observed at peak are associated with clinically meaningful antianginal and anti-ischemic effects, whereas concentrations obtained at trough were not.

Based on the results of the present experiment, the threshold plasma ranolazine free base concentration for anti-ischemic activity detected during ETT is likely to lie above about 550 ng per mL. Further, it is likely that ranolazine plasma concentrations must be maintained at or above the threshold value throughout the dosing interval to ensure antianginal and anti-ischemic activity during exercise throughout this interval.

Ranolazine was well tolerated over the plasma concentrations achieved in the present study. The rate of occurrence of adverse events did not differ among the ranolazine dosing regimens and placebo, and there were no drug-related changes in ECG intervals or complex morphology. In addition, there were no clinically significant changes in blood glucose concentrations, lipid values or liver function tests, suggesting that the metabolic effect of ranolazine does not extend to systemic glucose regulation or lipid metabolism.

Ranolazine improves exercise parameters with no detectable effect on heart rate and blood pressure in patients with chronic stable angina pectoris. It is likely that a threshold ranolazine plasma concentration above about 550 ng per mL must be obtained to detect these antianginal and anti-ischemic effects. Ranolazine is well tolerated over a wide range of plasma concentrations. Further study using larger doses of a sustained release preparation are warranted to fully evaluate this novel metabolic concept for management of ischemia.

Example 5

I. In vitro Comparison of IR Formulation and SR Formulations

The IR Formulation prepared according to Example 1 and the SR Formulations prepared according to Examples 2A–2C were tested in a USP Apparatus 2 dissolution tester, using 900 mL of 0.1 M hydrochloric acid as the dissolution fluid to simulate dissolution in the stomach.

TABLE 4

| Time | Percentage of Formulation Dissolved | | | |
|---|---|---|---|---|
| | Formulation | | | |
| (hours) | IR | A | B | C |
| 0.25 | 88.1 | | | |
| 0.5 | 100.5 | 13.9 | 17.6 | 17.5 |
| 1 | 101.7 | 19.9 | 26.0 | 25.7 |
| 2 | | 27.8 | 47.5 | 35.9 |
| 4 | | 39.0 | 69.2 | 48.4 |
| 8 | | 52.4 | 90.1 | 64.7 |
| 12 | | 61.6 | 99.6 | 74.2 |
| 24 | | 80.8 | 105.6 | 95.4 |

The tabular results show that while the IR Formulation is completely dissolved in no more than 0.5 hours (as expected for an immediate release formulation), SR Formulations A, B, and C displayed a prolonged dissolution of a low pH, as is desirable for a sustained release formulation.

II. In vivo Comparison of IR Formulation and SR Formulations A, B, and C

Single doses of the IR Formulation prepared according to Example 1 and SR Formulations A and B prepared according to Example 2 were administered to eleven healthy volunteers and their plasma concentrations of ranolazine free base were measured at 0, 20, 40, 60, 90, and 120 minutes, hourly to six hours, twice-hourly to eighteen hours, and at twenty-four hours after administration (SR Formulations only). The results are set forth in Table 5 below.

TABLE 5

| | Formulation | | | |
|---|---|---|---|---|
| | IR | A | B | C |
| $C_{max}$ (ISD) (ng/mL) | 1940 (807) | 753 (264) | 657 (316) | 925 (747) |
| $C_{trough}$ (ISD) (ng/mL) | 165 (111) | 158 (114) | 182 (110) | 290 (163) |
| $T_{max}$ (ISD) (hours) | 1.27 (0.5) | 4.09 (1.14) | 4.05 (1.31) | 6.55 (2.93) |
| $AUC_{0-24}$ (ISD) (ng.hr/mL) | 6530 | 5640 | 5280 | 5820 |

From Table 5 it is apparent that SR Formulations A, B and C of this invention exhibit dissolution properties which make them suitable for twice daily administration of ranolazine.

Example 6

This Example details a single-ascending dose, crossover-design study that assessed the safety and pharmacokinetic profile of single oral dose of ranolazine base SR Formulation of Example 2D. Human subjects were divided into three groups. Group 1 received 500, 750 and 1000 mg ranolazine SR. Group 2 received 1250 and 1750 mg ranolazine SR. Group 3 received 1500 and 2000 mg ranolazine SR. Each group also had a randomized placebo phase. Mean pharmacokinetic parameters following single oral doses of the ranolazine SR does are detailed in Table 6 below:

TABLE 6

Mean ± SD Pharmacokinetic Parameters (n = 8 except* n = 7)

| Dose SR (mg) | Group | $C_{max}$ (ng/mL) | $C_{trough}$ (ng/mL) | $T_{max}$ (hr) | $AUC_{0-30\ th}$ (ng.hr/mL) |
|---|---|---|---|---|---|
| 500 | 1 | 883 ± 353 | 382 ± 251 | 4.63 ± 1.19 | 9380 ± 4250 |
| 750 | 1 | 1300 ± 1060 | 455 ± 353 | 4.25 ± 0.886 | 12500 ± 9000 |
| 1000 | 1* | 1610 ± 959 | 695 ± 438 | 5.71 ± 2.14 | 18100 ± 9630 |
| 1250 | 2 | 2210 ± 716 | 943 ± 541 | 6.21 ± 3.52 | 25000 ± 8090 |
| 1500 | 3 | 1980 ± 1050 | 1070 ± 754 | 4.75 ± 0.886 | 25400 ± 16000 |
| 1750 | 2 | 3670 ± 1570 | 2400 ± 1260 | 5.25 ± 2.31 | 49200 ± 18200 |
| 2000 | 3 | 2440 ± 1120 | 1640 ± 937 | 5.21 ± 2.30 | 35400 ± 19100 |

The pharmacokinetic results reported in Table 6 indicate that ranolazine was slowly released from the SR formulation, and consequently the absorption of ranolazine was dissolution-rate limited. This resulted in prolonged plasma drug concentration-time profiles observed at all dose levels, with peak plasma levels at 4 to 6 hours post dose. Over the dose range 500 to 2000 mg, the mean $C_{max}$ and $AUC_0\text{-}_{30hr}$ increased in an approximately dose-proportional manner, although there appeared to be some deviation from proportionality within Group 2.

Example 7

This Example details a double-blind, placebo-controlled, multiple ascending-dose, crossover-designed volunteer study, to evaluate bid dosing. Six subjects received 4 days dosing with ranolazine SR formulation prepared according to Example 2D at 500, 750, and 1000 mg bid, followed by a morning dose on Day 5. Pharmacokinetic results are reported in Table 7, below.

TABLE 7

Day 5 Ranolazine Pharmacokinetic Parameters (mean ± SD)

| Parameter | Ranolazine SR 500 mg bid (n = 7) | Ranolazine SR 750 mg bid (n = 7) | Ranolazine SR 1000 mg bid (n = 7) |
|---|---|---|---|
| $C_{max}$ (ng/mL) | 1760 ± 715 | 2710 ± 657 | 3660 ± 1090 |
| $T_{max}$ (hr) | 2.00 ± 1.15 | 4.33 ± 1.62 | 4.17 ± 2.48 |
| $C_{min}$ (ng/mL) | 585 ± 340 | 1260 ± 501 | 1960 ± 812 |

According to Table 7, ranolazine was slowly released from the SR formulation, and consequently the pharmacokinetics were dissolution-rate limited. This resulted in extended plasma drug concentration-time profiles at all dose levels, with peak plasma levels observed at 2 to 4 hours post dose.

These results indicate that useful ranolazine plasma levels can be achieved in humans with dosing of this SR formulation on a bid schedule.

Example 8

This Example evaluated the safety and tolerability of administering racemic ranolazine free base formulations as in Example 2D. The individual and mean concentrations of racemic ranolazine and its enantiomers, (R)-(+)-N-(2,6-dimethylphenyl)-4-[2-hydroxy-3-(2-methoxyphenoxy)-propyl]-1-piperazineacetamide, (S)-(−)-N-(2,6-dimethylphenyl)-4-[2-hydroxy-3-(2-methoxyphenoxy)-propyl]-1-piperazineacetamide in human plasma were also determined.

The study was performed with ascending doses of sustained release ranolazine dosage forms. Before and at intervals during and after the dosing period, blood samples were drawn for ranolazine assay and blood pressure, heart rate, ECG and symptoms were monitored throughout. Data summaries were reviewed after each phase before proceeding to the next phase of the study.

Eight subjects, all healthy male volunteers aged between 18 and 40 entered and all completed the study and were available for pharmacokinetic and safety analysis. The subjects were each given doses of the various types of ranolazine free base in the form of sustained release tablets including 500 mg and 750 mg tablets or with matching placebo as necessary (2×750 mg size plus 1×500 mg size) to make unit oral doses of 1500 and 2000 mg.

In each phase: one dose bid for four days with a single dose on Day 5. On day 5 each volunteer underwent a full pharmacokinetic profile including supine and erect blood pressure (BP) and heart rate, ECG data, adverse events, clinical chemistry and hematology results, urinalysis results.

Steady state was tested for in each dose level, using $C_{48h}$, $C_{72h}$ and $C_{96h}$ and log transformed data, by analysis of covariance and by testing whether the coefficient for time was significantly different (defined as p<0.05) from 0. These tests were made using two-sided t-tests with estimates of variability from the ANOVA models. Steady state was also assessed by comparing means for $C_{48h}$, $C_{72h}$ and $C_{96h}$, using a mixed effects ANOVA model and untransformed and log, transformed data. For hemodynamic parameters, Day 1 predose treatment means and Day 5 data were compared across treatments via two-sided t-tests using estimates of variability from mixed effects ANOVA models. Ninety and 95% confidence intervals were calculated for the treatment comparisons. No adjustments were made for multiple comparisons.

The mean and standard deviation day 5 pharmacokinetic parameters of ranolazine free base are detailed in Table 8 below and the mean plasma profiles are shown in the figure. Steady-state plasma levels of ranolazine free base appeared to be attained by day 4. Within the dose interval there was a slow rise to maximum levels with $t_{max}$ values ranging from 1 to 6 h post-dose. Thereafter levels declined slowly, producing a small degree of fluctuation in plasma levels over the dosing interval. There appeared to be no differences in the pharmacokinetic parameters of the (+) R and (−) S enantiomers of ranolazine following multiple dosing with this SR formulation.

TABLE 8

Day 5 Racemic (RS), (+)R and
(−)S Ranolazine SR Pharmacokinetic Parameters

| Parameter | 1500 mg SR bid | | | 2000 mg SR bid |
| --- | --- | --- | --- | --- |
| | RS ranolazine | (+)R ranolazine | (−)S ranolazine | RS ranolazine |
| $C_{max}$ (ng/ml) | 5284 ± 2434 | 2909 ± 1308 | 2944 ± 1426 | 7281 ± 2700 |
| $C_{min}$ (ng/ml) | 2932 ± 1918 | 1436 ± 1046 | 1514 ± 1201 | 4149 ± 2228 |
| Median $t_{max}$ (h) | 4.00 | 4.00 | 4.00 | 4.00 |
| $C_{96h}$ (ng/ml) | 3656 ± 1918 | 2009 ± 1137 | 2399 ± 1205 | 5042 ± 1797 |

TABLE 8-continued

Day 5 Racemic (RS), (+)R and
(−)S Ranolazine SR Pharmacokinetic Parameters

| Parameter | 1500 mg SR bid | | | 2000 mg SR bid |
| --- | --- | --- | --- | --- |
| | RS ranolazine | (+)R ranolazine | (−)S ranolazine | RS ranolazine |
| $C_{108h}$ (ng/ml) | 2942 ± 1937 | 1447 ± 1071 | 1541 ± 1260 | 4398 ± 2396 |
| $AUC_{96-108h}$ (ng.h/ml) | 49516 ± 23945 | 25731 ± 13385 | 26407 ± 14849 | 68459 ± 25842 |
| $C_{ave}$ (ng/ml) | 4126 ± 1995 | 2144 ± 1115 | 2201 ± 1237 | 5705 ± 2153 |
| Degree of fluctuation | 0.664 ± 0.336 | 0.833 ± 0.402 | 0.824 ± 0.443 | 0.591 ± 0.240 |

Some subjects became too symptomatic on standing to complete BP measurements on ranolazine 1500 mg (n=3 of 8) and 2000 mg (n=2 of 8), usually 2–6 hours post-dose. Statistically significant reductions in orthostatic systolic BP were noted on day 5 on 1500 mg (−9.8 mm Hg; 4 hours post-dose) and 2000 mg (−8.4 mm Hg; 6 hours post-dose). Although the pattern of adverse events was similar on ranolazine and placebo, headache, dizziness and blocked nose seemed more common on ranolazine.

What we claim is:

1. A pharmaceutical dosage form comprising at least about 50 wt% ranolazine and the admixture of a pH-independent binder and a pH-dependent binder.

2. The pharmaceutical dosage form of claim 1 including from about 70 to about 80 wt% ranolazine.

3. The pharmaceutical dosage form of claim 1 wherein the pH dependent binder is methacrylic acid copolymer.

4. The pharmaceutical dosage form of claim 3 wherein the methacrylic acid copolymer is present in the pharmaceutical dosage form in an amount ranging from about 5 to about 12.5 wt%.

5. The pharmaceutical dosage form of claim 1 wherein the pH-independent binder is hydroxypropyl methylcellulose.

6. The pharmaceutical dosage form of claim 5 wherein the hydroxypropyl methylcellulose is present in the composition in an amount ranging from about 1 to about 3 wt%.

7. A pharmaceutical dosage form comprising from about 70 to about 80 wt% ranolazine and the admixture of from about 5 to about 12.5 wt% methacrylic acid copolymer and from about 1 to about 3 wt% hydroxypropyl methylcellulose, wherein the dosage form includes from about 350 to about 800 mg ranolazine.

8. The pharmaceutical dosage form of claim 7 including microcrystalline cellulose.

9. The pharmaceutical dosage form of claim 7 including magnesium stearate.

* * * * *

UNITED STATES PATENT AND TRADEMARK OFFICE
CERTIFICATE OF CORRECTION

| | | |
|---|---|---|
| PATENT NO. | : 6,503,911 B2 | Page 1 of 1 |
| APPLICATION NO. | : 10/041521 | |
| DATED | : January 7, 2003 | |
| INVENTOR(S) | : Andrew A. Wolff, Fiona Baker and John Richard Langridge | |

It is certified that error appears in the above-identified patent and that said Letters Patent is hereby corrected as shown below:

In column 11, line 22, "$\geq 3$ but $\geq 13$" should be -- $\geq 3$ but $\leq 13$ --.

Signed and Sealed this

Thirty-first Day of May, 2011

David J. Kappos
*Director of the United States Patent and Trademark Office*